United States Patent
Rauch

(10) Patent No.: US 9,192,486 B2
(45) Date of Patent: Nov. 24, 2015

(54) LOWER LIMB PROSTHESIS USABLE IN WATER ENVIRONMENT

(71) Applicant: Aqualeg SAS, Nantes (FR)

(72) Inventor: Frederic Rauch, Nantes (FR)

(73) Assignee: Aqualeg SAS, Nantes (FR)

( * ) Notice: Subject to any disclaimer, the term of this patent is extended or adjusted under 35 U.S.C. 154(b) by 0 days.

(21) Appl. No.: 13/900,999

(22) Filed: May 23, 2013

(65) Prior Publication Data

US 2014/0350695 A1 Nov. 27, 2014

(51) Int. Cl.
*A61F 2/60* (2006.01)
*A61F 2/78* (2006.01)
*A61F 2/76* (2006.01)
*A61F 2/50* (2006.01)

(52) U.S. Cl.
CPC ... *A61F 2/60* (2013.01); *A61F 2/76* (2013.01); *A61F 2/78* (2013.01); *A61F 2002/5001* (2013.01); *A61F 2002/501* (2013.01); *A61F 2002/505* (2013.01); *A61F 2002/5053* (2013.01); *A61F 2002/5056* (2013.01); *A61F 2002/5089* (2013.01); *A61F 2002/608* (2013.01); *A61F 2002/7837* (2013.01); *Y10T 409/303752* (2015.01)

(58) Field of Classification Search
CPC ............... A61F 2002/5001; A61F 2002/5089; A61F 2/78; A61F 2002/7837
USPC ................................. 623/27, 29, 32
See application file for complete search history.

*Primary Examiner* — Marcia Watkins
(74) *Attorney, Agent, or Firm* — Banner & Witcoff, Ltd.

(57) ABSTRACT

It concerns a prosthetic device for lower limb of a uses having a leg component, a foot component having a foot shell defining a first cavity within said foot shell and a coves component covering said leg component, said leg, foot and cover components being water compatible. The cover component is formed by an hollow flexible self-carrying sleeve defining a cavity within the sleeve around the leg component, the foot shell comprising a hole on its inner side, overlapping the sleeve on at least one centimeter and presenting an aperture below the sleeve to provide air communication between the cavity and the exterior. The cover component comprises in its upper part, a longitudinal slot, so that the water drains naturally from the first and second cavities.

10 Claims, 5 Drawing Sheets

LOWER LIMB PROSTHESIS USABLE IN WATER ENVIRONMENT

BACKGROUND OF THE INVENTION

1. Field of the Invention

The present invention is related to prostheses.

More particularly it concerns a prosthesis comprising covers and covers which can be used with lower limb prosthesis for everyday activities and water activities.

It also relates to a method of manufacturing such covers and/or prosthesis.

2. Description of Related Art

A typical walking leg prosthesis cannot be used in water since the component (feet, knees, adapters, foam covers) are not designed to be water resistant.

On the contrary the swim legs are disappointing for a user. They are sometimes functional, but have no cosmetic cover, and are often rudimentary both in terms of function and aesthetic.

The user is therefore not inclined to use them.

There is therefore an important need for a walking hybrid cover and/or prosthesis suitable for use in water for both above knee and below knee prosthetic device.

SUMMARY OF THE INVENTION

The present invention aims at solving this need by proposing a new prosthetic device which allows amputees to stroll along a beach, walk into the water, go for a swim and experience the waves just like everyone else and this at a very interesting cost and without sacrificing the aesthetic of the leg.

With the invention, the prosthesis has a cover which maintains its shape without the need for foam underneath.

The covers can be used and adapted to any parts or elements of existing walking prosthesis as long as such elements are water compatible.

With the invention, it is possible for the user to wear his everyday prosthesis, go to the bathroom, have a swim, enjoy kayaking, canoeing, sailing, white water rafting etc. and then resume his normal activities without the need to change his prosthesis.

And this is possible with a cosmetically appearing prosthesis.

Furthermore the whole device is easy to maintain as the cover can be removed from the mechanical parts of the prosthesis and reattached easily.

It can also be used with different prosthetic components and change from one to another, and/or easily adjusted to do so.

The invention comes from the observation that a traditional prosthesis buoyant or covered with foam not designed for immersion, meaning that it tends to float in the water. One of the ideas of the invention is therefore to propose a prosthesis with a cover which allows water to enter into the cover, to permit neutral buoyancy, which means that the leg will not have the tendency to float.

By achieving neutral buoyancy, the invention device can therefore be used for all types of water activities, including scuba diving.

When exiting from a pool or the ocean, the device of the invention is allowing a quick and discreet drain through the device, permitting the user to resume his normal activity immediately.

To achieve this aim the invention mainly proposes a prosthetic device for lower limb of a user comprising a tibial or femoral leg component, having a proximal end forming a socket to be connected to the stump of the user and a distal end, a foot component having a foot shell defining a first cavity within said foot shell and having an open upper part, said foot component being arranged to be articulated to the distal end of the leg component with adapters, and a cover component covering said leg component, said leg, foot and cover components being water compatible, wherein the cover component is formed by an hollow flexible self-carrying sleeve defining a second cavity within said sleeve around the leg component, said cover component being arranged to cooperate contiguously with the socket on one side and with the upper part of she foot shell on the other side on a predetermined height, said first cavity communicating with said second cavity, said foot shell comprising a hole on its inner side, said hole overlapping the sleeve on at least one centimeter and presenting an aperture below the sleeve extending until the top surface of the foot component (at the bottom of the foot shell) to provide air communication between the cavities and the exterior of the device, and wherein the cover component comprises in its upper part, close to the socket, a longitudinal slot comprising two contiguous lips for ventilation, so that the water drains naturally from the first and second cavities.

The invention also proposes additionally and/or alternatively the following embodiments:

the hole is a rectangle of width between 0.3 mm and 1 cm and advantageously 0.5 cm and of length between 2 cm and 5 cm, for instance 4 cm, with an overlapping with the sleeve of between 0.5 cm and 2 cm, for instance 1 cm;

the slot is of a length between 2 cm and 4 cm, for instance 3 cm;

the sleeve comprises an overlay of at least three layers, at least the external layer being transparent;

the sleeve comprises three parts, i.e.

a first part directed towards the foot which can be rolled back and which cooperates slight fittingly with the upper part of the foot shell, second part which is connected to the first part with bending capabilities and which is rigid or substantially rigid along the main central part of the leg component, and third part connected to the second part with bending capabilities (flexible), said third part cooperating contiguously with the socket of the leg component;

the sleeve is made of a superposition of layers, wherein at least one layer is a transparent or translucent silicone layer which forms the external layer of the sleeve, at least two layers of dyed elastic fabric, at least the elastic fabric closer to the external layer being light permeable.

Advantageously, the dyed elastic fabric layers are of two different colours.

The superposition of a transparent silicone layer with a layer of elastic fabric permits the mechanical resistance of the sleeve and gives the needed rigidity while authorizing, by modification of the thickness of the layers at different positions along the sleeve, its bending capacities.

The superposition of two layers of elastic fabric authorizes to modify the permeability to the light, which permits a great number of combinations while obtaining a particularly aesthetic result, mimicking particularly well a real skin.

In another advantageous embodiment, the sleeve comprises two layers of silicone sandwiching at least two layers of elastic fabric.

Advantageously the second layer of silicone is opaque.

Advantageously the sleeve further comprises at least a layer of painting between two layers of elastic fabric, for instance made of polyamide, having for instance between $1.10^3$ to $3.33 \cdot 10^{-3}$ g/m of fabric wires, preferably between $1.33\times10^{-3}$ g/m and $2.77\times10^{-3}$ g/m.

Also advantageously the device being for a femoral prosthesis, the sleeve comprises a folding ply below the knee part, for facilitating the folding of the knee component.

The invention also relates to a method for manufacturing covers for lower leg prosthesis as described here above.

It also concerns a method for manufacturing a cover for leg prosthesis of a user comprising the steps of:

taking digital pictures with a calibration pattern of the healthy limb (the sound limb) of a user and/or through a scanner allowing such calibration according to four directions (rear, front and lateral faces) such as the tibial and/or femoral parts of the healthy leg is precisely determined, transmitting and/or incorporating such digital pictures to a distal server via Internet together with references and specification of a leg and a foot components determined by the prosthesis maker of the user, (for instance obtained by scanning the prosthesis)

digitally reconstructing by symmetry (superposition) the external geometry of the missing leg of the user, designing by CADCAD the cover component taking the leg and foot components specifications into account, said leg component having an upper socket to be connected to the stump of the user and said foot component having an hollow foot shell, forming a plain model of said cover component with a robotic milling apparatus (for instance in plastic material such as polystyrene)

manufacturing the cover component, using said model as a support, by forming or depositing successive lay outs of plastic and/or textile on said support, in order to obtain multiple plastic and/or textile layers and therefore forming a sleeve defining a cavity, peeling or extracting the sleeve from the support, cutting in the foot shell a hole of at least 0.5 cm of width on its inner side, said hole being placed in a position such as the sleeve overlaps said hole on an height of at least one centimeter and presents an aperture below the sleeve and towards the bottom of the foot shell when in place on an height of at least two centimeters and, cutting a slot comprising two contiguous lips in the upper part of the cover component, so that the water drains naturally from the cavities of the cover and leg components.

Advantageously the cut in the upper part of the cover component is undertaken after putting in place said cover component on the leg and foot components.

In an advantageous embodiment, the manufacturing of the sleeve comprises the following steps:

(a) putting an elastic fabric casing jacket on the plain model to form a first elastic fabric layer, (b) covering said casing jacket with a layer of silicone, (c) repeating steps (a) at least twice and step (b) at least once for forming said sleeve, for obtaining at least a superposition of layers as follows, from the external part of the sleeve towards the internal part, a transparent or translucid silicone layer, at least two elastic fabric layers, one silicone layer and at least one elastic fabric layer.

The invention will be better understood by referring to the following description of embodiments given without limitation by way of example.

BRIEF DESCRIPTION OF THE SEVERAL VIEWS OF THE DRAWINGS

The description is related to the accompanying drawings, in which.

DETAILED DESCRIPTION OF THE INVENTION

Figure 1:
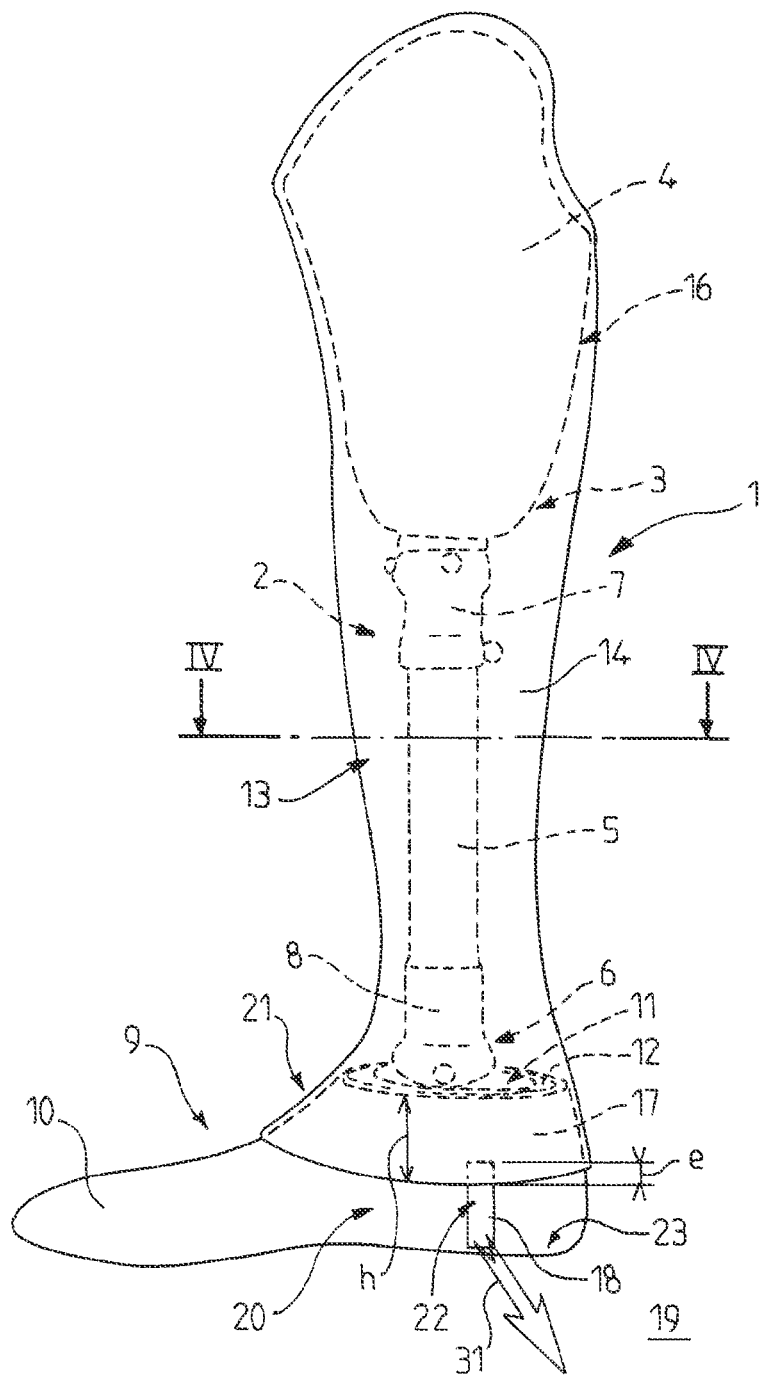
FIG. 1 is a first lateral view of the embodiment of the invention more particularly described here.
Figure 2:
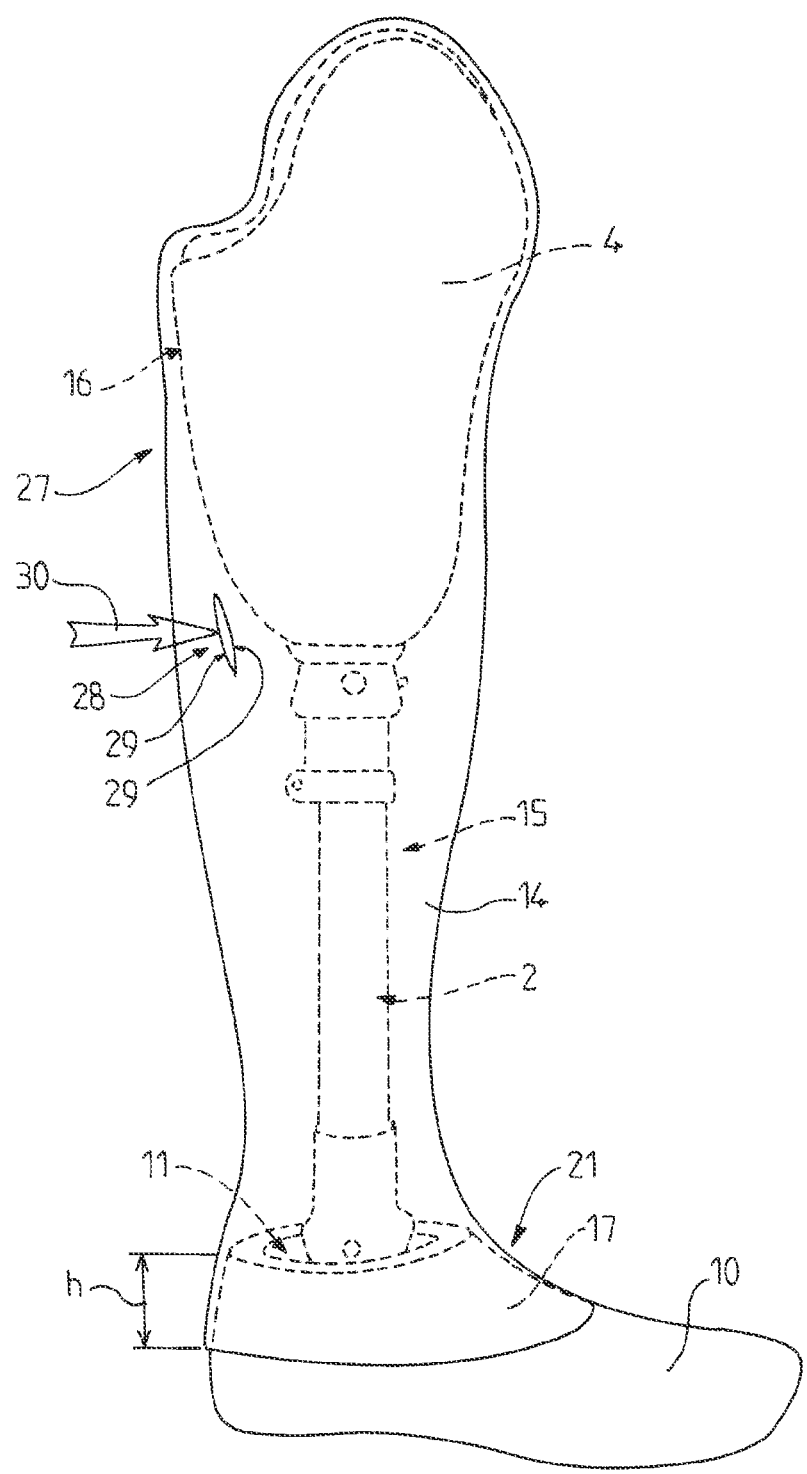
FIG. 2 is a second lateral view of the prosthesis on the other side of FIG. 1.

FIGS. 1 and 2 show a prosthetic device 1 for lower limb of a user comprising a tibial leg component 2 (dashed line). The tibial leg component 2 has a proximal end 3 forming a socket 4 to be connected to the stump of the user (not shown), said socket being connected to a pylon 5 by adapters 7, said pylon 5 having a distal end 6 presenting an adapter 8.

The device further comprises a foot component 9 articulated to the distal end 6 of the pylon by the adapter 8.

The foot component 9 comprises a foot shell 10 defining a first cavity 11 with an open upper part 12.

The device comprises additionally a cover component 13 formed by an hollow flexible self-carrying sleeve 14 defining a second cavity 15 in communication with the first cavity (by the upper part 12 of said first cavity) and surrounding the leg component 2.

The cover component 13 is arranged to cooperate continuously (tight fitting junction 16) with the socket 4 on one side.

It cooperates with the upper part 17 of the foot shell 10 on the other side, substantially on a predetermined height h.

The foot shell 10 (see also FIG. 3) comprises a hole 18 making the interior of the first cavity 11 communicate with the exterior 19 of the device, and situated on his inner side 20.

The hole 13 is overlapping the lower part 21 of the sleeve 14 on at least a distance e of one cm and presents an aperture 22 below the sleeve extending to the top surface 23 of an interior of the first cavity or a bottom surface of the foot component 9 (see FIG. 3) or to provide air communication between the cavities and the exterior 19 (arrows 24).

Some leaks (arrows 25) will also exist on the periphery 26 of the lower part 21.

The cover component 13 (see FIG. 2) additionally comprises in its upper part 27, close to the socket, a longitudinal slot 28 comprising two contiguous lips 29 for ventilation (see arrow 30), so that the water drain naturally (arrow 31—FIG. 1) and immediately from the first and second cavities, when the user get out of the water.

Figure 4:
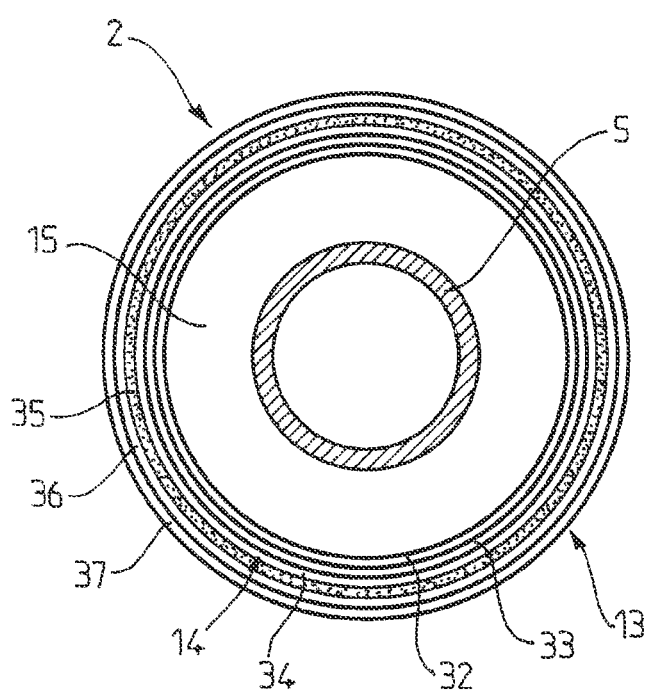
FIG. 4 is a section view along IV-IV of the prosthesis of FIG. 1.

FIG. 4 shows a cross section view along IV-IV of the sleeve 14 of the embodiment of the invention more particularly described here.

The sleeve 14 comprises an internal layer 32 in elastic fabric such as tubular nyglas from the company Otto Bock reference 623T9 and then, from the internal part of the sleeve towards the external part, an opaque silicone layer 33, an elastic dyed fabric layer 34, a (misty) layer of paint 35, an elastic dyed layer 36 permeable to the light, and an external transparent silicone layer 37, each layer being of thickness corresponding to the requested rigid or bending (flexible) qualities of the sleeve at its different parties.

Figure 5:
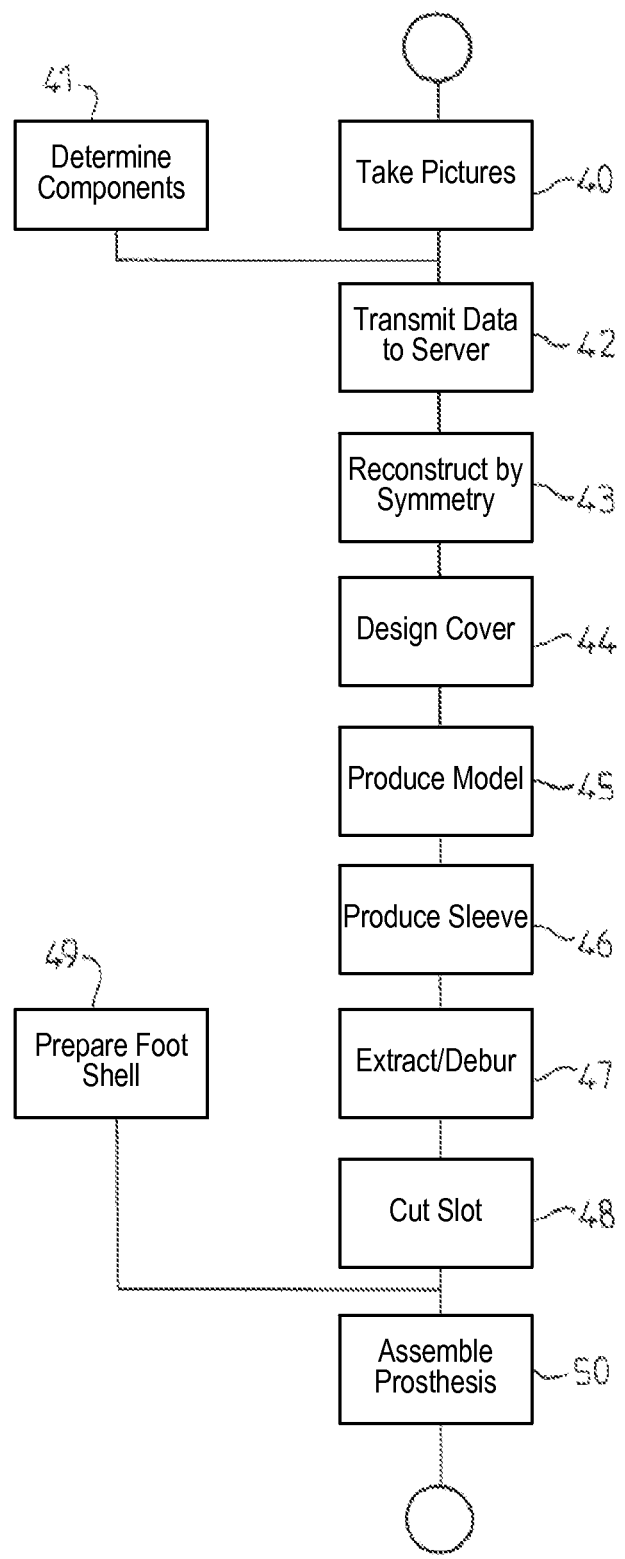
FIG. 5 shows schematically the different steps of the method of the invention as more particularly described here.

FIG. 5 shows the different steps so follow for manufacturing the sleeve of the prosthesis according to the embodiment of the invention more particularly described here.

After taking digital pictures with a calibration pattern of the sound limb of the user (step 40) according to four directions (front, rear and lateral faces) and determining the leg and foot components (step 41) for his client, the prosthesis maker transmits the data to a distal server (step 42).

The leg and foot components are water compatible and are chosen in a way known per se by the man skilled in the art in the catalogues of the prosthesis manufacturers. They are for example manufactured from titanium parts and carbon fiber blades.

The data received are then used for digitally reconstructing by symmetry (step 43) the external geometry of the missing leg while taking care of the adaptation with the foot component.

The file is then used for designing (step 44) by CADCAD the cover (step 44) using known software such as the software known as Solid Works by the US firm Solid Works.

The result is transmitted to a milling apparatus which produces (step 45) a plain model which will be a support for the sleeve to manufacture.

The following step 46 is to produce the sleeve by forming or depositing successively on the support, layers of elastic fabric, silicone and/or painting, for instance in successive operations provided automatically and/or manually.

When the sleeve is finished, it is kept for drying and then extracted from its support and prepared (deburred) in step 47.

The sleeve is then put into place and the slot is cut at the top of the sleeve (step 48).

Parallely, the foot shell is prepared by cutting the aperture in its lateral part (step 49).

Figure 6:
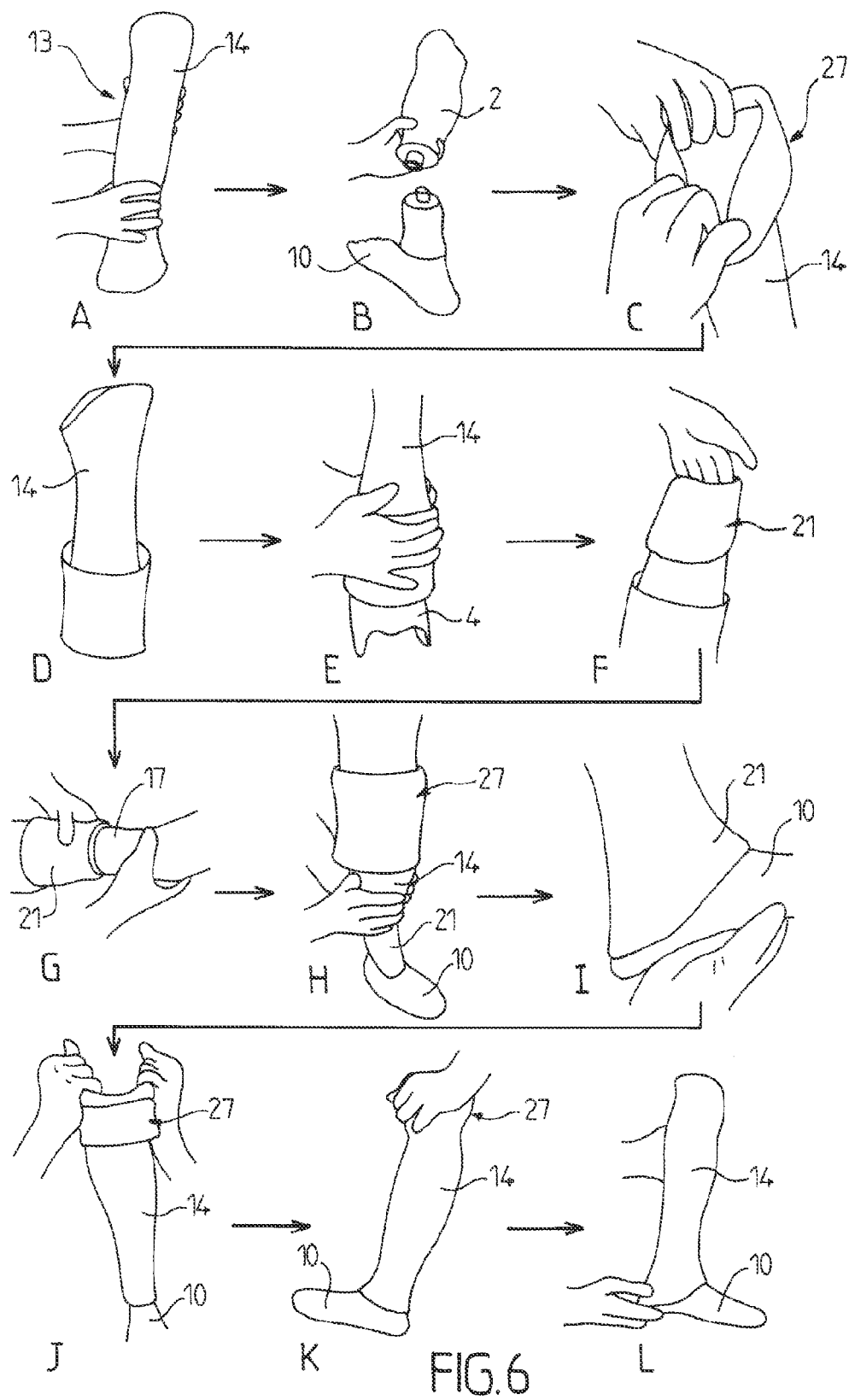
FIG. 6 illustrates the different steps undertaken to build the prosthesis.

Then the prosthesis is assembled (step 50) as described in reference to FIG. 6 (step A to L).

Figure 3:
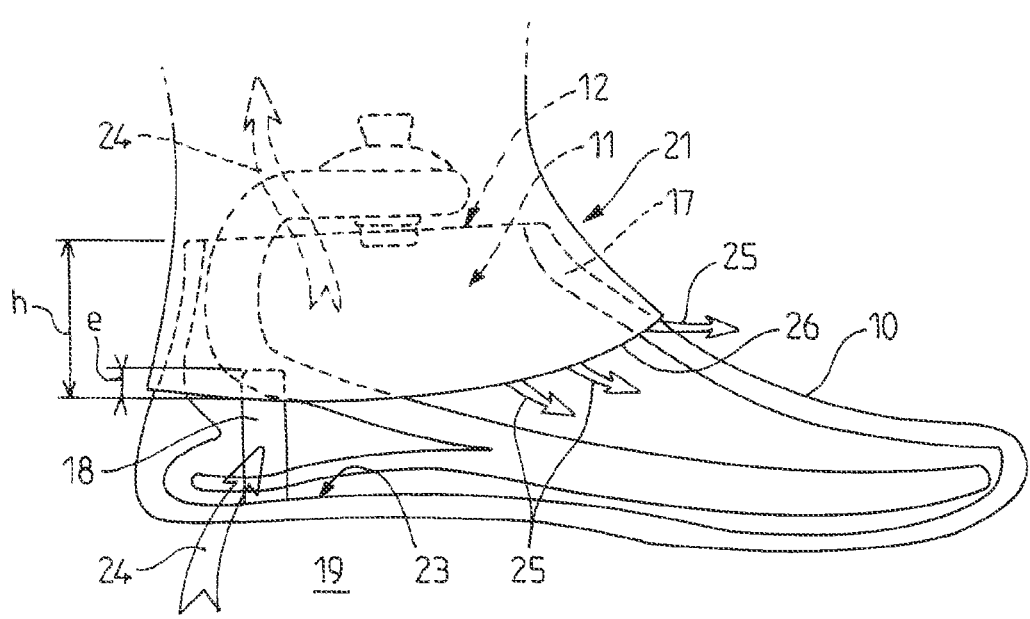
FIG. 3 is a lateral view of the foot component with its foot shell, according to an embodiment of the invention.

The numbers of reference are the same than the ones used in reference to FIG. 1-3.

Parting from the sleeve 14 of the cover member 13 (A) and after assembling the foot member 10 on the leg member 2 together (B), the sleeve is prepared by returning the (soft) upper part 27 of the sleeve (C) which is put upside down (D) and introduced on the socket 4 of the leg member (E).

The lower part 21 of the sleeve is then returned (F) (thanks to its bendable or flexible character) and put into place on the foot upper part 17 (G) to be jointly adapted (H) to it, for obtaining the configuration (I).

The upper part 27 of the sleeve is then put in place (J and k) to obtain the prosthesis according to the embodiment of the invention more particularly described here.

The invention claimed is:

1. A prosthetic device for a lower limb of a user comprising a tibial leg component, having a proximal end forming a socket to be connected to a stump of the user and a distal end, a foot component having a foot shell defining a first cavity within said foot shell and having an open upper part, said foot component being arranged to be articulated to the distal end of the leg component with adapters, and a cover component covering said leg component, wherein said tibial leg component, foot component and cover component are water compatible, wherein the cover component is formed by an hollow flexible sleeve defining a second cavity within said sleeve around the leg component, said cover component being arranged to cooperate contiguously with the socket on one side and with the upper part of the foot shell on the other side by a predetermined overlapping height h, wherein said first cavity communicates with said second cavity, wherein said foot shell comprises a hole on its inner side, said hole overlapping the sleeve by at least one centimeter and presenting an aperture below the sleeve extending to a top surface of an interior of the first cavity of the foot component to provide air communication between the cavities and outside of the device, and wherein the cover component comprises in its upper part, close to the socket, a longitudinal slot comprising two contiguous lips for ventilation, the two contiguous lips arranged to allow water to drain naturally from the first and second cavities when the device has been immerged in and then extracted from water.

2. A prosthetic device according to claim 1, wherein the hole is a rectangle having a width between 0.3 mm and 1 cm and having a length between 2 cm and 5 cm, with the overlapping with the sleeve being between 0.5 cm and 2 cm.

3. A prosthetic device according to claim 2, wherein said width is 0.5 cm.

4. A prosthetic device according to claim 1, wherein the slot has a length between 2 cm and 4 cm.

5. A prosthetic device according to claim 4, wherein the sleeve is made of a superposition of layers, wherein at least one layer is a transparent or translucent silicone layer which forms an external layer of the sleeve, at least two layers are of dyed elastic fabric, and elastic fabric of the one of the at least two layers closer to the external layer is transparent or translucent.

6. A prosthetic device according to claim 5, comprising a second layer of silicone, wherein the second layer of silicone is opaque.

7. A prosthetic device according to claim 5, wherein the sleeve further comprises at least a layer of painting between said two layers of elastic fabric.

8. A prosthetic device according to claim 1, wherein the sleeve comprises at least three successive layers, the at least three successive layers comprising a transparent external layer.

9. A prosthetic device according to claim 1, wherein the sleeve comprises three parts, the three parts comprising a first part directed towards the foot foot component which can be rolled up and which tightly and fittingly cooperates with the upper part of the foot shell, a second part which is connected to the first part and which is rigid or substantially rigid along a main central part of the leg component and a third part connected to the second part, said third part cooperating with the socket of the leg component.

10. A prosthetic device according to claim 1 wherein the sleeve comprises two layers of silicone sandwiching at least two layers of elastic fabric.

\* \* \* \* \*